(12) United States Patent
Austin

(10) Patent No.: US 9,782,556 B2
(45) Date of Patent: Oct. 10, 2017

(54) CPAP HOSE HANGER AND METHOD OF USE

(71) Applicant: AG Industries LLC, St. Louis, MO (US)

(72) Inventor: Gary Austin, Euclid, OH (US)

(73) Assignee: AG Industries LLC, St. Louis, MO (US)

(*) Notice: Subject to any disclaimer, the term of this patent is extended or adjusted under 35 U.S.C. 154(b) by 669 days.

(21) Appl. No.: 14/205,020

(22) Filed: Mar. 11, 2014

(65) Prior Publication Data

US 2014/0283885 A1   Sep. 25, 2014

Related U.S. Application Data

(60) Provisional application No. 61/775,770, filed on Mar. 11, 2013.

(51) Int. Cl.
  *A61M 39/08*   (2006.01)
  *A61M 16/08*   (2006.01)

(52) U.S. Cl.
  CPC ..... *A61M 16/0875* (2013.01); *A61M 2209/08* (2013.01)

(58) Field of Classification Search
  CPC .................................................. A61M 39/08
  See application file for complete search history.

(56) References Cited

U.S. PATENT DOCUMENTS

2002/0120224 A1* 8/2002 Zia ..................... A61M 5/1418
                                                          604/6.16

* cited by examiner

*Primary Examiner* — Jason Ko
(74) *Attorney, Agent, or Firm* — Michael J. Berchou, Esq.; Timothy W. Menasco, Esq.; Harter Secrest & Emery LLP

(57) ABSTRACT

A tube cleaning apparatus for cleaning a CPAP hose or other hose including a trough for receiving a tube therein, the trough curving downwardly from an apex to an engagement mechanism associated with each opposite end portion of the trough for hanging the hose therefrom, the opposite end portion of the hose being engageable with the engagement mechanism for allowing the hose to soak with a cleaning solution therein, and the hose being receivable within the trough with its opposite end portions extending downwardly from the apex for drying purposes.

9 Claims, 3 Drawing Sheets

CPAP HOSE HANGER AND METHOD OF USE

CROSS-REFERENCE TO RELATED APPLICATION

This application claims priority to U.S. Provisional patent application Ser. No. 61/775,770, filed Mar. 11, 2013, the entire disclosure of which is hereby incorporated by reference herein.

BACKGROUND OF THE DISCLOSURE

This disclosure relates generally to a hose hanger and, more particularly, to a hose hanger for use with a continuous positive airway pressure (CPAP) hose.

CPAP therapy uses a machine to help a person who has obstructive sleep apnea (OSA) to breathe more easily during sleep.

As a treatment or therapy for OSA, CPAP therapy uses a mild air pressure to keep an airway open. CPAP therapy typically is used for people who have breathing problems, such as OSA. CPAP therapy also may be used to treat preterm infants whose lungs have not yet fully developed. For example, physicians may use CPAP therapy to treat infants who have respiratory distress syndrome or bronchopulmonary dysplasia. In some preterm infants whose lungs have not fully developed, CPAP therapy improves survival and decreases the need for steroid treatment for their lungs.

CPAP therapy for in-home use utilizes a machine specifically designed to deliver a constant flow of air or constant air pressure. Some CPAP machines have other features as well, such as heated humidifiers. CPAP therapy is the most effective treatment for OSA in which the mild pressure from the CPAP machine prevents the airway from collapsing or becoming blocked.

However, mucus and moisture built-up in an enclosed space of a CPAP hose can contribute to the growth of mold, algae and/or other unhealthy agents. In addition, a layer of sediment can accumulate over time inside a standard CPAP hose between uses. Thus, there is a present need to effectively clean the internal surface of the standard hose used in CPAP therapy. Currently, most users slosh a soapy solution or soak the hose and then follow with a rinse and dry. This method is messy due to the length of the hose involved and due to the fact that it is hard to dry the hose when cleaning is completed. Another method is to soak the hose in a vinegar solution. Again, this method is cumbersome due to the length of the hose involved. Yet another method is to use a brush with a soapy solution, a vinegar solution or any suitable cleaning solution. However, with all these methods, there still needs to be an efficient and easy means to soak the hose in a cleaning solution followed by an easy and efficient means to both rinse and dry the hose.

Therefore, it would be advantageous to provide means for soaking, cleaning and rinsing a CPAP hose followed by means for drying the hose.

BRIEF SUMMARY OF THE DISCLOSURE

One aspect of the present disclosure is a tube cleaning apparatus including a trough for holding a tube therewithin wherein the tube can be attached to the apparatus for cleaning and soaking purposes and wherein the tube can be positioned within the trough for drying purposes. The trough is sandwiched by two side wall brackets which help retain the tube within the trough when positioned therewithin. The apparatus may include a removably attachable hook member attachable to at least one side wall bracket or a removably attachable suction cup attachable to the outer side portion of one of the side wall brackets. The hook member can be used to hang the apparatus from any suitable member such as a towel bar or shower rod, or the suction cup can be used to attach the apparatus to any suitable surface. The present apparatus further includes a first cut-out or other engagement means located at one end of the trough and a second cut-out or other engagement means located at the opposite end of the trough, the trough curving downward from its apex towards each opposite end portion. The CPAP tube has a cuff associated with each opposite end which is engageable with both the first and second cut-outs for hanging the hose therefrom. A pair of first and second end cap members can be inserted into the opposite end portions of the hose for sealing a cleaning solution therewithin. The end caps each include a ring or opening for receiving a pair of hooks associated with one of the side wall brackets.

Another aspect of the present disclosure is a method for cleaning a CPAP tube using the above referenced tube cleaning apparatus. The cleaning method includes filling a tube with a cleaning solution, attaching an end cap to each end of the tube, agitating the tube, hanging the ends of the tube from the engagement means located at the respective ends of the trough, soaking the tube while hanging, removing the tube from the apparatus, removing the end caps either before or after soaking, emptying the cleaning solution from the tube, and draping the tube over the trough of the tube cleaning apparatus.

Another aspect of the present disclosure is a system for cleaning a tube including assembling a hose hanger, cleaning a hose, and drying a hose, all in conjunction with using the present hose hanger.

BRIEF DESCRIPTION OF THE DRAWINGS

For a better understanding of the present disclosure, reference may be made to the present accompanying drawings.

DETAILED SUMMARY OF THE DISCLOSURE

Figure 1:
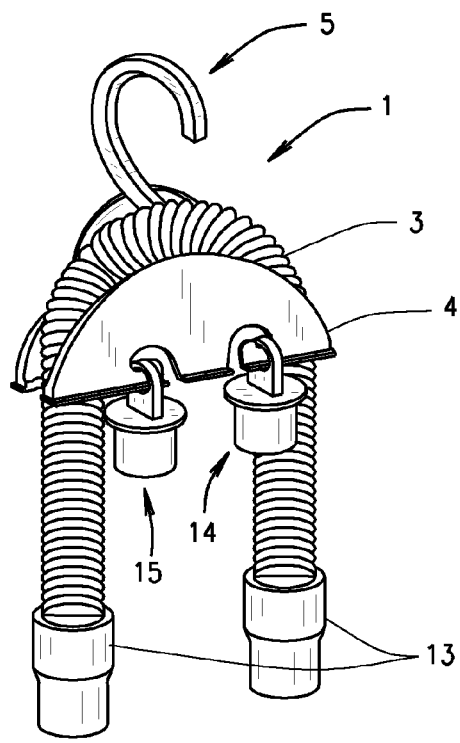
FIG. 1 is a perspective view of the present hose hanger with a hose positioned within the trough and hanging therefrom, the hose hanger being constructed in accordance with the teachings of the present invention.

Referring to FIGS. 1-8, one aspect of the present disclosure is a tube cleaning apparatus or hangar 1 comprising a trough 2 wherein a tube 3 can be balanced and held within the trough. The tube 3 can be a CPAP tube used for CPAP treatment or therapy. The trough 2 is sandwiched by two side wall brackets 4. A hook member 5 can be attached to one side wall bracket 4 by inserting a base member 6 of the hook 5 into a slot 7 (FIGS. 3 and 6) located at the top center of one of the side wall brackets 4. The hook 5 can be hung from a towel bar, a shower rod, or any other suitable member. A suction cup 8 (FIG. 3) can also be attached to the outer side of one of the side wall brackets 4 by inserting a central hub member 9 associated with the suction cup 8 into a second slot or opening 10 associated with one of the side wall brackets 4 and thereafter pushing the central hub member 9 upward into the narrow portion of opening 10 thereby snapping it into a holding position. The suction cup 8 can be adhered to any suitable surface.

Figure 4:
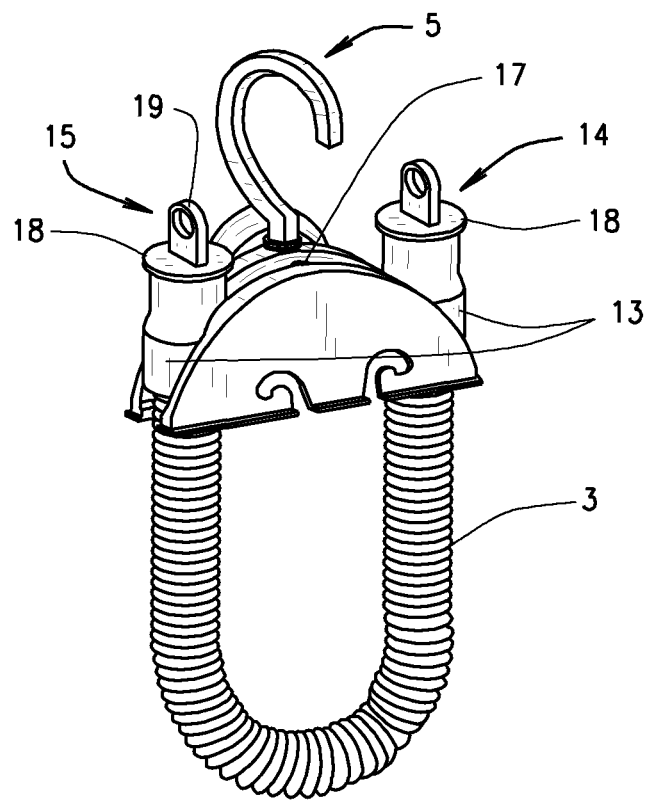
FIG. 4 is a perspective view of the present hose hanger with the hose hanging from the side of the hanger with the cuffs of the hose resting within cut-outs associated with the present hose hanger.

As best illustrated in FIGS. 2, 3, 7 and 8, the trough 2 curves downward from an apex 17 forming an arched shaped or curved bridge which extends to a first cut-out 11 on a first side of the trough 2 and to a second cut-out 12 on a second side thereof. The cut-out 11 includes a ridge 11A and the cut-out 12 includes a ridge 12A. Each cut-out also includes a pair of detents 11B and 12B located at the mouth or opening to each cut-out. A CPAP tube 3 or other tube can engage and can be supported within the first and the second cut-outs 11 and 12 on the ridges 11A and 12A as shown in FIG. 4. A cuff 13 associated with each of the tube end portions (FIG. 1) can engage and rest upon or within either the first or the second cut-outs 11 and 12 on the respective first and second ridges 11A and 12A. A first end cap 14 can be inserted into one end of the tube 3 and a second end cap 15 can be inserted into the other end of the tube. Each end cap 14 and 15 also includes a shoulder 18. If necessary, depending upon the size of the tube 3, the shoulder 18 can also engage and/or rest upon or within either of the cut-outs 11 and 12 on the respective ridges 11A and 12A.

Figure 2:
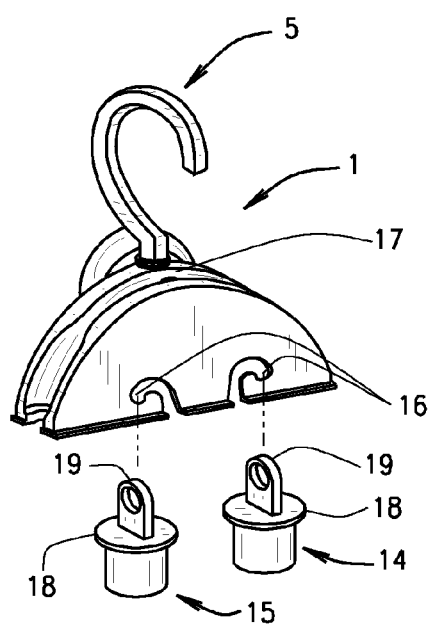
FIG. 2 is an exploded perspective view of the two end caps separated from the hooks associated with the present hose hanger.
Figure 3:
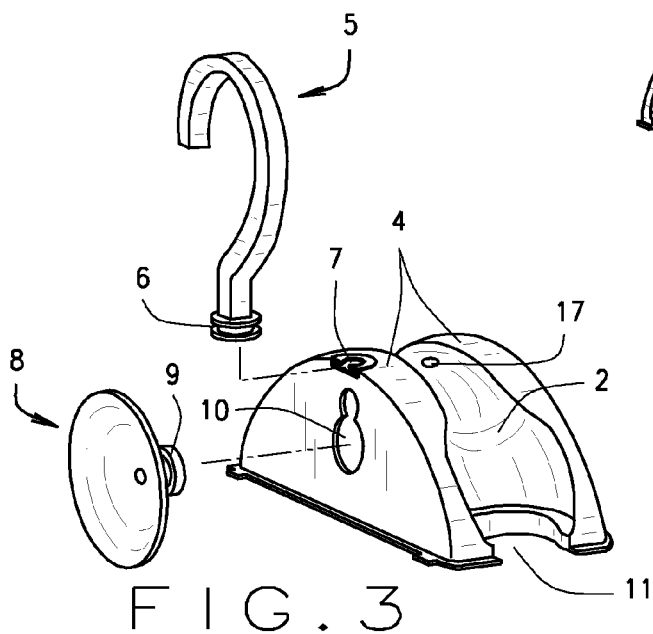
FIG. 3 is an exploded perspective view of the hook member and the suction cup separated from the present hose hanger.
Figure 5:
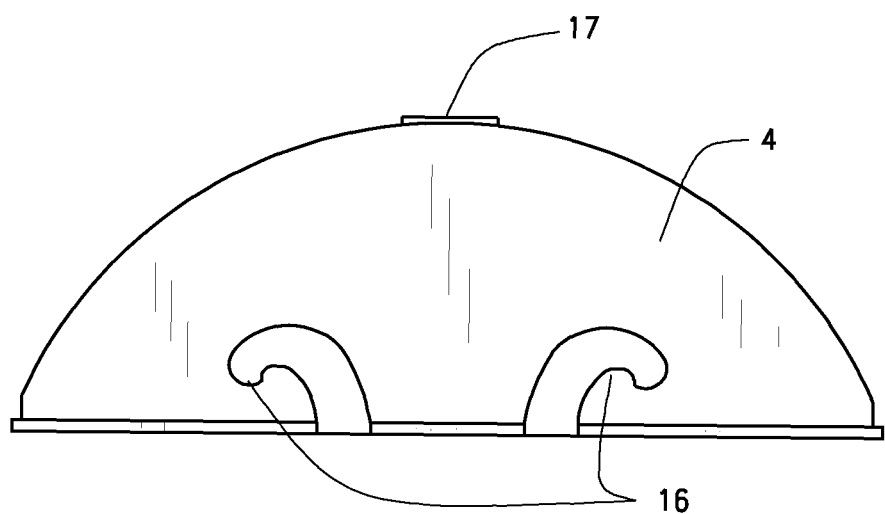
FIG. 5 is a front elevational view of the hose hanger illustrating the hooks for holding the hose end caps.
Figure 6:
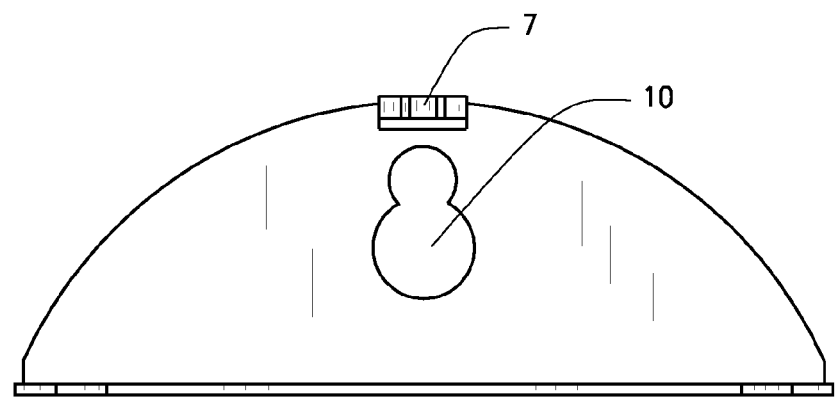
FIG. 6 is a rear elevational view of the hose hanger illustrating the slot for the hook member and the opening for engaging the suction cup.
Figure 7:
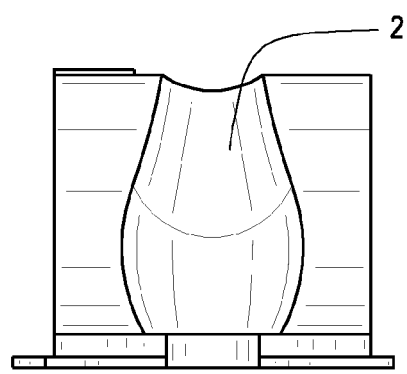
FIG. 7 is a side elevational view of the present hose hanger illustrating the trough and the cut-out associated with one side of the hose hanger.
Figure 8:
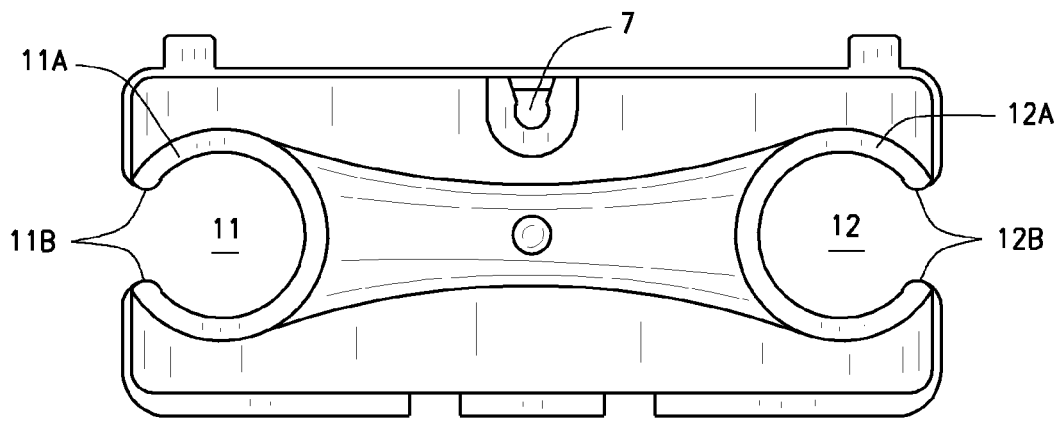
FIG. 8 is a top plan view of the present hose hanger.

Two hooks 16 are formed into or located on one side of one of the side wall brackets 4 as shown in FIGS. 2 and 5. A first end cap 14 and a second end cap 15 can be hung from the respective hooks 16 as shown in FIGS. 1 and 2 through the use of a ring 19 associated with each end cap 14 and 15. The hooks 16 can be cut outs formed in the side wall bracket 4 and the ring 19 can be inserted within the hook cut outs 16 for hanging therefrom.

Detents 11B and 12B are an integral feature of the present device. The spacing of the two detents at the opening to the cut-outs 11 and 12 on each side are generally smaller than the outside diameter of the hose itself. This feature forces the user to apply a small pressure on the hose to insert it into the respective cut-out which then constrains or locks the hose into the cut-out. Without this feature the hose may have a tendency to slide downward on one side or the other if not placed centrally. Also, many hoses have a natural curvature somewhere along the length of the hose as a result of the typical packaging of the hose product prior to sale. The memory of the hose may try to force the hose into a more open or spread configuration which will then allow the hose to become displaced from the arc support or ridges 11A and 12A. The sizing of the through diameter, detent grips and shoulder diameter all work in conjunction to maintain the hose in a secure manner in either hose orientation. There may be times when a hose will have an end cuff of a different configuration than what the through channel yokes or cut-outs 11 and 12 were intended such as 15 mm slim hoses. Because all CPAP hoses have been engineered to fit an industry standard 22 mm tapered port, the inclusion of the shoulder 18 on the end caps 14 and 15 complement the design and allow the shoulder of the cap to supplement the need for the shoulder of the hose cuff.

Another aspect of the present disclosure is a method for cleaning a CPAP tube. The method includes filling a tube 3 with a cleaning solution, attaching an end cap 14, 15 to each end of the tube, agitating the tube, attaching the cuffs 13 to the cut-outs 11 and 12 as shown in FIG. 4 for soaking the tube, removing the tube 3 and end caps 14, 15 from the cut-outs 11 and 12, emptying the cleaning solution from the tube, and draping the tube over the trough 2 of a tube cleaning apparatus for drying as shown in FIG. 1.

Another aspect of the present disclosure is a system for cleaning a tube which includes assembling the hose hanger 1, cleaning a hose 3, and then drying the hose. The tube is a CPAP tube. The assembling of the cleaning system includes sliding a base 6 of a hook member 5 into a slot 7 at the top of the hose hanger 1, or sliding a central hub member 9 of a suction cup 8 into a slot 10 on one side portion of the hose hanger 1 and pushing the hub member 9 upward into a narrower slot portion for holding the same, and hanging or attaching the hose hanger 1 via either the hook member 5 or the suction cup 8 from or to a suitable member. The cleaning process includes attaching the hose 3 to the hose hanger 1 by attaching the cuffs 13 of the hose to the cut-outs 11 and 12, with the open ends of the hose facing up as shown in FIG. 4, pouring a suitable cleaning solution into the hose, inserting end caps 14 and 15 into each end of the hose, removing the hose from the hose hanger, raising and lowering each end of the hose allowing the cleaning solution to thoroughly agitate and clean the inside of the hose, reattaching the cuffs 13 to the cut-outs 11 and 12 as shown in FIG. 4 to allow for soaking of the tube for a pre-determined period of time, removing the end caps 14 and 15, discarding the cleaning solution, and rinsing the hose. The drying process includes checking that the hose is free of cleaning solution or soaking solution, inverting the hose over the hose hanger 1 by placing the hose in the trough 2, storing the end caps 14 and 15 on hooks 16, and allowing the hose to dry.

Abbreviated instructions for the assembly and use of the present hose hanger are as follows.

Assembly:

1) Slide the base of the hook attachment into the slot at the top of the hanger and snap firmly in place to allow the hose hanger to be hung from a towel bar or a shower rod; OR 2) Slide the hub of the suction cup attachment into the slot on the back of the hanger and push upward snapping in place to allow the hose hanger to be adhered to a clean smooth surface. Press the cup firmly to the smooth surface and verify proper suction by lightly pulling downward on the hanger; no movement should occur.

Cleaning:

1) Snap CPAP hose into the hanger with cuffs resting on the lips or cut-outs and the open ends facing up.

2) Pour a hose manufacturer recommended cleaning solution into the hose until ½-⅔ full.

3) Insert the end caps firmly into each end of the CPAP hose.

4) Remove hose from hanger and briskly raise and lower each end of the hose to allow the solution to clean the inside of the hose.

5) Remove end caps, discard cleaning solution, and rinse hose thoroughly of any remaining solution.

6) Continue to "soaking" or continue to "drying".

Soaking:

1) Snap CPAP hose back into hanger with cuffs resting on the lips or cut-outs and the open ends facing up.

2) Pour a hose manufacturing recommended soaking solution into the hose until full and replace end caps.

3) Leave hose on hanger and allow soaking for 30 minutes or a time period recommended by the manufacturer. Do not support the hose with the end cap hangers attached to the hooks.

4) Discard soaking solution, rinse hose thoroughly to remove any remaining solution and continue to "drying".

Drying:

1) Make sure CPAP tube is free of cleaning solution and has been rinsed.

2) Invert CPAP hose over the hose hanger and snap in place into the trough and store end caps on cap hooks.

3) Allow hose to hang inverted until dry.

Moreover, unless defined otherwise, all technical and scientific terms used herein have the same meaning as commonly understood by a person of ordinary skill in this art. Although any methods and materials similar to or equivalent to or those described herein can be used in the practice or testing of the present disclosure, the preferred methods and materials are described above.

Thus, there has been shown and described several embodiments of a novel CPAP Hose Apparatus/Hanger which fulfills the objects and advantages sough therefor. Many changes, modifications, variations and other uses and applications of the present invention will, however, become apparent to those skilled in the art after considering this specification and accompanying drawings. All such changes, modifications, variations and other uses and applications which do not depart from the spirit and scope of the present invention are deemed to be covered by the present invention and all equivalents therefor, which is limited only by the claims which follow.

The invention claimed is:

1. A tube cleaning apparatus comprising a trough sandwiched between two side wall brackets for receiving a tube therein, the trough having opposite end portions including a first cut-out located on a first side of the trough and a second cut-out on a second side of the trough, the first cut-out and the second cut-out for hanging a tube therefrom, a tube having opposite end portions and being engageable with the first cut-out and the second cut-out to allow the tube to soak with a cleaning solution therein, the tube being further receivable within the trough with its opposite end portions extending downwardly for drying, wherein said trough curves downward from an apex to said first and second cut-outs wherein each opposite end of the tube includes a cuff, each cuff being removably attachable to said first or second cut-out, such that the cuffs rest on the cut-outs and the open ends of the tube face up, for soaking of the tube.

2. The tube cleaning apparatus of claim 1 including a hook member removably attachable to at least one of the side wall brackets.

3. The tube cleaning apparatus of claim 2 wherein the hook member includes a base member and is attachable to said at least one side wall bracket by inserting said base member into a slot associated with said at least one side wall bracket.

4. The tube cleaning apparatus of claim 1 including a suction cup removably attachable to at least one of the side wall brackets.

5. The tube cleaning apparatus of claim 4 wherein said suction cup includes a central hub member and is attachable to said at least one side wall bracket by inserting said central hub member into an opening associated with the outer side of said at least one side wall bracket.

6. The tube cleaning apparatus of claim 1 wherein said first and second cut-outs each include a ridge, and wherein the respective cuffs rest upon said respective ridges.

7. The tube cleaning apparatus of claim 1 wherein said first and second cut-outs each include a pair of detents, and wherein the opposite end portions of a tube is insertable between said respective pairs of detents.

8. The tube cleaning apparatus of claim 1 including a first end cap removably insertable into one end of the tube and a second end cap removably insertable into the other end of the tube.

9. The tube cleaning apparatus of claim 8 including a pair of hooks on one side of at least one of said side wall brackets for receiving said first and second end caps.

* * * * *